(12) United States Patent
Kurosawa et al.

(10) Patent No.: US 9,022,947 B2
(45) Date of Patent: May 5, 2015

(54) RESPIRATION IMPEDANCE MEASURING DEVICE AND RESPIRATION IMPEDANCE DISPLAY METHOD

(75) Inventors: Hajime Kurosawa, Sendai (JP); Yoshio Shimizu, Sendai (JP); Toshiaki Hoki, Tokyo (JP)

(73) Assignees: Chest M.I. Incorporated, Tokyo (JP); Tohoku Techno Arch Co., Ltd., Sendai-shi, Miyagi (JP)

( * ) Notice: Subject to any disclaimer, the term of this patent is extended or adjusted under 35 U.S.C. 154(b) by 407 days.

(21) Appl. No.: 13/264,075

(22) PCT Filed: Apr. 12, 2010

(86) PCT No.: PCT/JP2010/056541
§ 371 (c)(1),
(2), (4) Date: Dec. 12, 2011

(87) PCT Pub. No.: WO2010/119843
PCT Pub. Date: Oct. 21, 2010

(65) Prior Publication Data
US 2012/0101400 A1    Apr. 26, 2012

(30) Foreign Application Priority Data
Apr. 13, 2009  (JP) ................................ 2009-097028

(51) Int. Cl.
*A61B 5/085*    (2006.01)
*A61B 5/08*    (2006.01)
(Continued)

(52) U.S. Cl.
CPC .............. *A61B 5/0809* (2013.01); *A61B 5/038* (2013.01); *A61B 5/087* (2013.01); *A61B 5/682* (2013.01); *A61B 5/7257* (2013.01); *A61M 2230/46* (2013.01)

(58) Field of Classification Search
CPC .............................. A61B 5/0809; A61B 5/087
USPC .................................................. 600/529–543
See application file for complete search history.

(56) References Cited

U.S. PATENT DOCUMENTS 6,443,907 B1 * 9/2002 Mansy et al. ................. 600/529
7,662,101 B2 * 2/2010 Lee et al. ...................... 600/484
(Continued)

FOREIGN PATENT DOCUMENTS

JP  3-39140   2/1991
JP  3-116807  12/1991
(Continued)

OTHER PUBLICATIONS

International Search Report issued by the Japanese Patent Office on Jun. 1, 2010, for International Application No. PCT/JP2010/056541.

*Primary Examiner* — Jacqueline Cheng
*Assistant Examiner* — Puya Agahi
(74) *Attorney, Agent, or Firm* — Finnegan, Henderson, Farabow, Garrett & Dunner, L.L.P.

(57) ABSTRACT

Continuous measurement of breathing impedance with extremely high precision is enabled by executing noise elimination. A loudspeaker applies an air vibration pressure by an oscillation wave to an oral cavity, the oscillation wave being obtained by frequency-cuffing so executed that the oscillation wave has only the frequency component that is left after the culling is executed from a plurality of different frequencies and being generated by a pulse signal for pulse drive with pulses made positive and negative separately in correspondence to the time of exhalation and the time of inhalation. A pressure inside the oral cavity is detected and a breathing flow is detected, and a signal obtained by the detection is Fourier-transformed to obtain a spectrum. Analysis of the spectrum is performed to obtain breathing impedance.

10 Claims, 12 Drawing Sheets

(51) Int. Cl.
  *A61B 5/03* (2006.01)
  *A61B 5/087* (2006.01)
  *A61B 5/00* (2006.01)

(56) References Cited

U.S. PATENT DOCUMENTS 7,909,034 B2 * 3/2011 Sinderby et al. ......... 128/204.23

2008/0139956 A1 * 6/2008 Diong ........................ 600/533
2009/0062672 A1 3/2009 Sly et al.
2009/0326403 A1 * 12/2009 Bassin et al. ................ 600/538

FOREIGN PATENT DOCUMENTS

| JP | 2008-541957 | 11/2008 |
| JP | 2009-240752 | 10/2009 |
| WO | WO 2006/130922 A1 | 12/2006 |

* cited by examiner

FIG 2
(a)
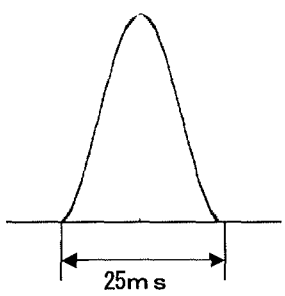
25ms
(b)
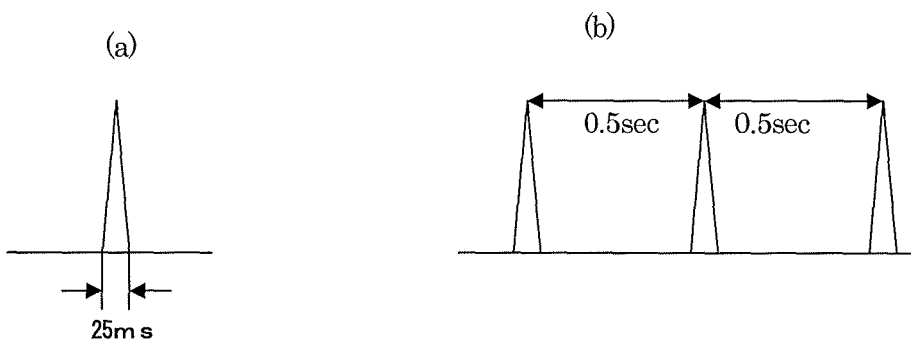
0.5sec    0.5sec
FIG 3
25ms (a)

(b)

(c)

(d)

(e)

(a)

(b)

(c)

FREQUENCY: : 1Hz/DIV
Rrs, Xrs:1cmH2O(1/s)・DIV
TIME SCAL : 0.5sec/DIV

F I G 1 9

| RESISTANCE [cmH2O/(L/s)] | | | |
|---|---|---|---|
| | max | min | sub |
| R5 | 5.63 | 1.18 | 4.45 |
| R20 | 3.72 | 1.27 | 2.45 |
| R5-R20 | 1.91 | -0.09 | 2.00 |
| Rres | 4.72 | 1.22 | 3.50 |

| Fres[Hz] | 12.63 |
|---|---|

RESPIRATION IMPEDANCE MEASURING DEVICE AND RESPIRATION IMPEDANCE DISPLAY METHOD

TECHNICAL FIELD

The present invention relates to a respiratory impedance measuring apparatus and method that are capable of continuously measuring a respiratory impedance of a human being, etc., and to a respiratory impedance display method.

BACKGROUND ART

Conventionally, an apparatus of this kind is known that includes a sine-wave pressurizing apparatus to apply as a load a sine-wave air vibration pressure to a respiratory system, an air current velocity detector to detect an air current velocity of the respiratory system, an air pressure detector to detect an air pressure of the respiratory system, and a resistance computing unit that calculates breathing resistance from the air current velocity and the air pressure detected by the air current velocity detector and the air pressure detector.

The conventional apparatus: further includes a reference signal converter to convert a signal of the sine-wave air vibration pressure that is applied by the sine-wave pressurizing apparatus into a reference signal and a vector computing device that processes a signal of the air current velocity using the reference signal of the sine-wave air vibration pressure from the reference signal converter and that, thereby, takes out only a component at the same frequency as that of the reference signal; and is adapted to calculate the breathing resistance using the resistance computing unit from the signal of the air current velocity obtained by the vector computing device and the signal of the air pressure detected by the air pressure detector.

As above, this apparatus is adapted to measure the breathing resistance using the resistance computing unit from the signal of the air current velocity obtained by the vector computing device and the signal of the air pressure detected by the air pressure detector and, therefore, noises may be removed even when the amount of ventilation of the breathing is a little and the number of ventilating sessions is large. Therefore the apparatus has an advantage that the apparatus may execute high precision measurement of breathing resistance (see Patent Document 1).

However, the removal of the noises is not sufficient even by the conventional apparatus and realization of a higher-performance respiratory impedance measuring apparatus is demanded.

CITATION LIST

Patent Literature

Patent Literature 1: Japanese Patent Application KOKAI Publication No. H03-039140.

DISCLOSURE OF THE INVENTION

Problems to be Solved by the Invention

The present invention was conceived in view of the current circumstances in breathing impedance measurement and an object thereof is to provide a breathing impedance measuring apparatus and a breathing impedance displaying method that enable breathing impedance measurement with extremely high precision and that may be widely applied to determination of respiratory system diseases.

Means for Solving the Problem

The breathing impedance measuring apparatus according to the present invention characteristically includes: a pressurizing means that applies an air vibration pressure to the inside of an oral cavity; a pressure detecting means that detects the pressure of the inside of an oral cavity; a flow detecting means that detects a flow generated by breathing; a control means that causes the air vibration pressure to be generated by an oscillation wave that is a pulse signal to drive the pressurizing means with pulses made positive and negative separately in correspondence to the time of breathing and the time of exhaling and that is a pulse signal obtained by frequency-culling so executed that the signal has only the frequency component that is left after the culling is executed from a plurality of different frequencies; a Fourier transforming means that obtains signals obtained by the pressure detecting means and the flow detecting means under a pressurized condition provided by the pressurizing means, and that Fourier-transforms the obtained signals to obtain a spectrum; an extracting means that obtains a breathing high frequency component based on a spectrum that corresponds to a frequency component culled from the result of the transformation by the Fourier transforming means, and that takes out an oscillation wave component by subtracting the breathing high frequency component from a spectrum that corresponds to a frequency component left by the culling; and a computing means that divides a pressure component by a flow component for each frequency for the result of extraction by the extracting means.

The breathing impedance measuring apparatus according to the present invention is characterized in that the control means causes the air vibration pressure to be generated by the oscillation wave having only the $n/T_1$ (n: an integer, $T_1$: a real number) frequency component, by giving a pulse wave having a cycle $T_1$ as the frequency culling.

The breathing impedance measuring apparatus according to the present invention is characterized in that the control means includes a signal input means that supplies an input signal to the pressurizing means so that an oscillation wave having a desired pressure waveform is an output signal, based on reverse computation using the input signal and the output signal of the pressurizing means and a transfer function of the pressurizing means.

The breathing impedance measuring apparatus according to the present invention is characterized in that the signal input means supplies a signal obtained by adding a specific value to each of frequency components of a signal obtained by the reverse computing or by reverse computing a signal formed by adding an impulse to an onset portion of the output signal, as an input signal to the pressurizing means.

The breathing impedance measuring apparatus according to the present invention is characterized in that signal processing is carried out in a signal processing section $T_2$ ($T_2 = mT_1$ (m denotes an integer of 1 or larger)).

The breathing impedance displaying method according to the present invention is characterized in that, in a breathing impedance displaying method of executing display on a displaying apparatus based on breathing impedance measured by the breathing impedance measuring apparatus, three-dimensional display is executed by three-dimensionally taking breathing impedance values based on an impedance axis, a frequency axis, and a time axis, that an image is created by including breathing impedance obtained by executing an interpolation process on culled frequencies in the three-dimensional display to execute the display, and that a flow waveform obtained by a flow detecting means that detects an exhalation flow and an inhalation flow is displayed together with the impedance.

The breathing impedance displaying method according to the present invention is characterized in that the display is executed by distinguishing periods of exhalation and periods of inhalation from each other by color as vertical strips of different colors at the background of a screen.

The breathing impedance displaying method according to the present invention is characterized in that breathing impedance vales in a plurality of times of breathing are averaged for each elapsed time to determine averages, which are displayed as a three-dimensional image, that the averages at a given number of frequencies are each displayed as a line segment, and that maximums, minimums, and differences between the maximums and the minimums at the given number of frequencies are determined and are displayed in the form of characters.

The breathing impedance displaying method according to the present invention is characterized in that the display is executed by creating an image whose length in the direction of the time axis is determined to be the length long enough to repeat therein at least two sets of exhalation and inhalation.

The breathing impedance displaying method according to the present invention is characterized in that the display is executed by creating an image that expresses the magnitude of an impedance value using variation in color and/or in light and shade.

Effects of the Invention

According to the present invention: an air vibration pressure by an oscillation wave that is frequency-culled is applied to the inside of an oral cavity; the pressure of the inside of the oral cavity is detected; the flow of breathing is detected; a spectrum is obtained by Fourier-transforming these signals detected; a breathing high frequency component that contributes as a noise is obtained using a spectrum that corresponds to a frequency component culled from the result of the Fourier transformation; the breathing high frequency component is subtracted from a spectrum that corresponds to the frequency component left by the culling; thereby, an oscillation wave component is extracted; computing is executed of dividing a pressure component by a flow component for each of frequencies for the result of this extraction; and, thereby, breathing impedance is obtained. Therefore, the breathing impedance may be obtained using the oscillation wave component from which the breathing high frequency component is securely removed. In addition, a pulse signal is adopted for generating the air vibration pressure by the oscillation wave in pulse drive such that pulses are made positive and negative separately in correspondence to the time of exhalation and the time of inhalation. Breathing resistance, therefore, may be measured under the same physiological condition in periods of exhalation and in periods of inhalation, so that breathing impedance measurement with extremely high precision is enabled through proper measurement.

According to the present invention: the air vibration pressure by the oscillation wave having only the $n/T_1$ (n: an integer, $T_1$: a real number) frequency components is caused to be generated by supplying the pulse having the cycle $T_1$; therefore, the breathing high frequency component is obtained using the spectrum that corresponds to the frequency component culled; and the breathing high frequency component is subtracted from the spectrum that corresponds to the frequency component left by the culling (frequency component other than the $n/T_1$ frequency component). Therefore, the breathing high frequency component is securely removed to enable the breathing impedance measurement with extremely high precision.

According to the present invention, a plurality of sine waves at a plurality of different frequencies are combined and, thereby, the air vibration pressure by the oscillation wave that is frequency-component-culled is caused to be generated. As a result, only the breathing high frequency component is included in the spectrum that corresponds to the frequency component culled. Therefore, a breathing high frequency component included in an oscillation signal may be estimated from this breathing high frequency component signal. Hence the breathing high frequency component may securely be removed using this estimated signal to enable the breathing impedance measurement with extremely high precision.

According to the present invention, an input signal is supplied to a pressurizing executing portion such that the oscillation wave having a desired pressure waveform is the output signal based on the reverse computation using the input signal and the output signal for the pressurizing and a transfer function of the pressurizing executing portion. Therefore, the measurement may be executed using the oscillation wave having the desired pressure waveform and respiratory impedance measurement with extremely high precision is enabled.

According to the present invention, the input signal is the signal obtained by adding a specific value to each of the frequency components of the signal obtained by the reverse computing, or by reverse computing the signal formed by adding an impulse to the onset portion of the output signal. Therefore, the signal waveform of the result of the reverse computing may be stabilized and, thereby, the measurement using the oscillation wave having a desired waveform may be executed and the respiratory impedance measurement with extremely high precision is enabled.

According to the present invention, signal processing is executed in a signal processing section $T_2$ ($T_2=mT_1$ (m denotes an integer of 1 or larger)). As a result, the spectrum that corresponds to the frequency component left by the culling and the spectrum that corresponds to the frequency component culled are obtained properly to be able to execute a necessary process.

According to the breathing impedance displaying method of the present invention, in the breathing impedance displaying method of executing display on a displaying apparatus based on the breathing impedance measured by the breathing impedance measuring apparatus, three-dimensional display is executed by three-dimensionally taking values based on the impedance axis, the frequency axis, and the time axis, an image is created by including breathing impedance obtained by executing an interpolation process on the culled frequency in the three-dimensional value display to execute the display, and a flow waveform obtained by a flow detecting means that detects an exhalation flow and an inhalation flow is displayed together with the impedance. Because the result of the interpolation process is also displayed as an image, variation in impedance values is minutely and smoothly displayed, which enables properly grasping impedance for the whole of frequencies, as the flow waveform formed of the exhalation flow and the inhalation flow is also displayed. Hence the breathing impedance displaying method may widely be applied to determination of respiratory system diseases.

According to the breathing impedance displaying method of the present invention, the display is executed by distinguishing periods of exhalation and periods of inhalation from each other by color as vertical strips of different colors at the background of a screen. As a result, the periods of exhalation and periods of inhalation are displayed to be quite obvious in displaying the breathing impedance, which is convenient for determination of respiratory system diseases, etc.

According to the breathing impedance displaying method of the present invention, breathing impedance vales in a plurality of times of breathing are averaged for each elapsed time to determine averages, which are displayed as a three-dimensional image, the averages at a given number of frequencies are each displayed as a line segment, and maximums, minimums, and differences between the maximums and the minimums at the given number of frequencies are determined and are displayed in the form of characters. Hence breathing impedance values that vary at each cycle of breathing are averaged and are obtained in the form of characters, which are convenient for comparison, etc.

According to the respiratory impedance display method according to the present invention, the display is executed by creating the image with the length in the direction of the time axis that is a length long enough to repeat therein at least two sets of exhalation and inhalation. Therefore, not an observation of a sudden variation but an observation having a specific span is enabled and, thereby, proper observations may be secured.

According to the breathing impedance displaying method of the present invention, the display is executed by creating an image that expresses the magnitude of an impedance value using variation in color and/or in light and shade. As a result, the magnitude of the impedance value may easily be recognized in a quite obvious manner, which is expected to be extremely helpful to various researches and examinations based on breathing impedance and to visual explanations (appeals) to patients.

BRIEF DESCRIPTION OF DRAWINGS

FIG. 2 is a diagram depicting one example of triangular pulse waves that are oscillation waves used in the breathing impedance measuring apparatus according to the embodiment of the present invention;

FIG. 3 is a diagram depicting one example of a Hanning pulse wave that is an oscillation wave used in the breathing impedance measuring apparatus according to the embodiment of the present invention;

FIG. 19 is a diagram depicting one example in which based on the displayed example of FIG. 18, maximums, minimums, and differences between the maximums and the minimums at the given number of frequencies are determined and are displayed in the form of characters.

DESCRIPTION OF EMBODIMENT

Figure 1:
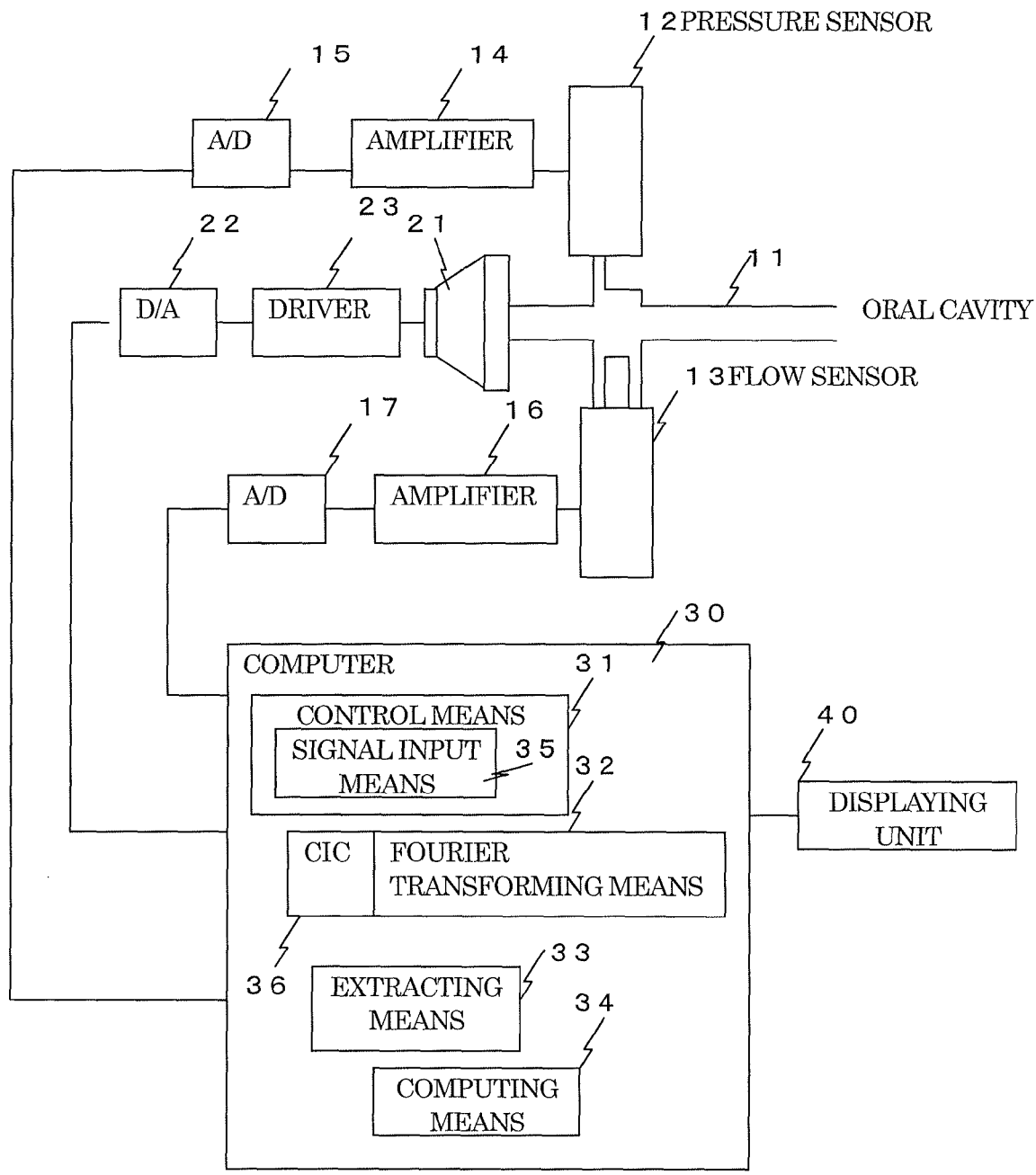
FIG. 1 is a configuration diagram of a breathing impedance measuring apparatus according to an embodiment of the present invention.

Embodiments of a respiratory impedance measuring apparatus and method according to the present invention will be described with reference to the accompanying drawings. FIG. 1 is a diagram of the configuration of the embodiment of the respiratory impedance measuring apparatus according to the present invention. The respiratory impedance measuring apparatus includes as its main components: a tube 11 whose tip is attached to an oral cavity of a human and through which a breathing flow flows; a pressure sensor 12 that is attached to the tube 11 and that makes up a pressure detecting means to detect the pressure in the oral cavity; a flow sensor 13 that makes up a flow detecting means of detecting the flow of breathing at the same position as that of the pressure sensor 12; a loudspeaker 21 that makes up a pressurizing means to apply an air vibration pressure to the inside of the oral cavity; and a computer 30.

An output signal of the pressure sensor 12 is amplified by an amplifier 14, is digitized by an A/D converter 15, and is taken in by the computer 30. An output signal of the flow sensor 13 is amplified by an amplifier 16, is digitized by an A/D converter 17, and is taken in by the computer 30.

The computer 30 includes a control means 31, a Fourier transforming means 32, an extracting means 33, and a computing means 34. The control means 31 includes a signal input means 35. The control means 31 outputs a signal driving the loudspeaker 21 that is the pressurizing means and causes the air vibration pressure by an oscillation wave having only odd-number frequency components or even-number frequency components, to be generated. An output of the control means 31 is converted into an analog signal by a D/A converter 22 and is sent to a driver 23. The driver 23 drives the loudspeaker 21 and, thereby, the air vibration pressure is applied to the inside of the oral cavity.

In the above, the control means 31 causes the air vibration pressure by the oscillation wave having $n/T_1$ (n: an integer, $T_1$: a real number) frequency components, to be generated by giving a pulse wave having the cycle of $T_1$ second (frequency-culling). Though various waveforms may be considered as the pulse wave, for example, as depicted in FIG. 2(a), a triangular pulse has the temporal width of about 25 ms at the base level. When this triangular pulse is output with the cycle $T_1$ that is, for example, $T_1$=0.5 second, a triangular pulse wave having a spectrum of 2, 4, 6, 8 Hz, . . . may be given (FIG. 2(b)). When the triangular pulse is output with the cycle $T_1$ that is, for example, $T_1$=0.333 second, a triangular pulse wave having a spectrum of 3, 6, 9, 12 Hz, . . . may be given. The triangular pulse can be output with the cycle $T_1$ that is, for example, $T_1$=0.25 second. In this case, a triangular pulse wave having a spectrum of 4, 8, 12, 16 Hz, . . . may be given.

As depicted in FIG. 3, a Hanning pulse as another example has the temporal width of about 25 ms at the base level. A pulse wave using this pulse is created and output similarly to the case of the triangular pulse wave.

The signal input means 35 included in the control means 31 supplies an input signal to the loudspeaker 21 such that an oscillation wave having a desired waveform is an output signal, based on reverse computing using an input signal and an output signal of the loudspeaker 21, and a transfer function of the loudspeaker 21.

In the above description, the relation between the pulse wave's being positive and negative and the direction of a flow (breathing flow) is physiologically significant. Now, it is assumed that in a flow curve, the direction of an exhalation flow in the negative area (projecting downward) and the direction of the pulse wave is the same to provide negative pulses (projecting downward). In this case, the flow is accelerated, thus increases its velocity. As a result, the internal pressure of the bronchus decreases due to the effect of the oscillation wave by the pulse wave, which causes the bronchus to reduce its radius. Hence resultant breathing resistance increases. When the negative pulses are used also at the time of inhalation, on the other hand, an inhalation flow is in the positive area of the flow curve, where the inhalation flow is in an upward direction opposite to the direction of the exhalation flow. The negative pulse wave thus acts in the direction of decelerating the flow, so that the internal pressure of the bronchus increases to cause the bronchus to expand its radius. Hence resultant breathing resistance decreases.

Generally, when pulses projecting in the same direction are used regardless of exhalation and inhalation, measured breathing resistance depends on the direction of the pulse wave applied as the oscillation wave against the direction of the breathing flow, which means the breathing resistance is measured under different physiological conditions for exhalation and inhalation. Hence correct measurement is not carried out. To avoid this, the control means 31 outputs the pulse wave with its pulses made positive and negative separately in correspondence to exhalation and inhalation.

Figure 4:
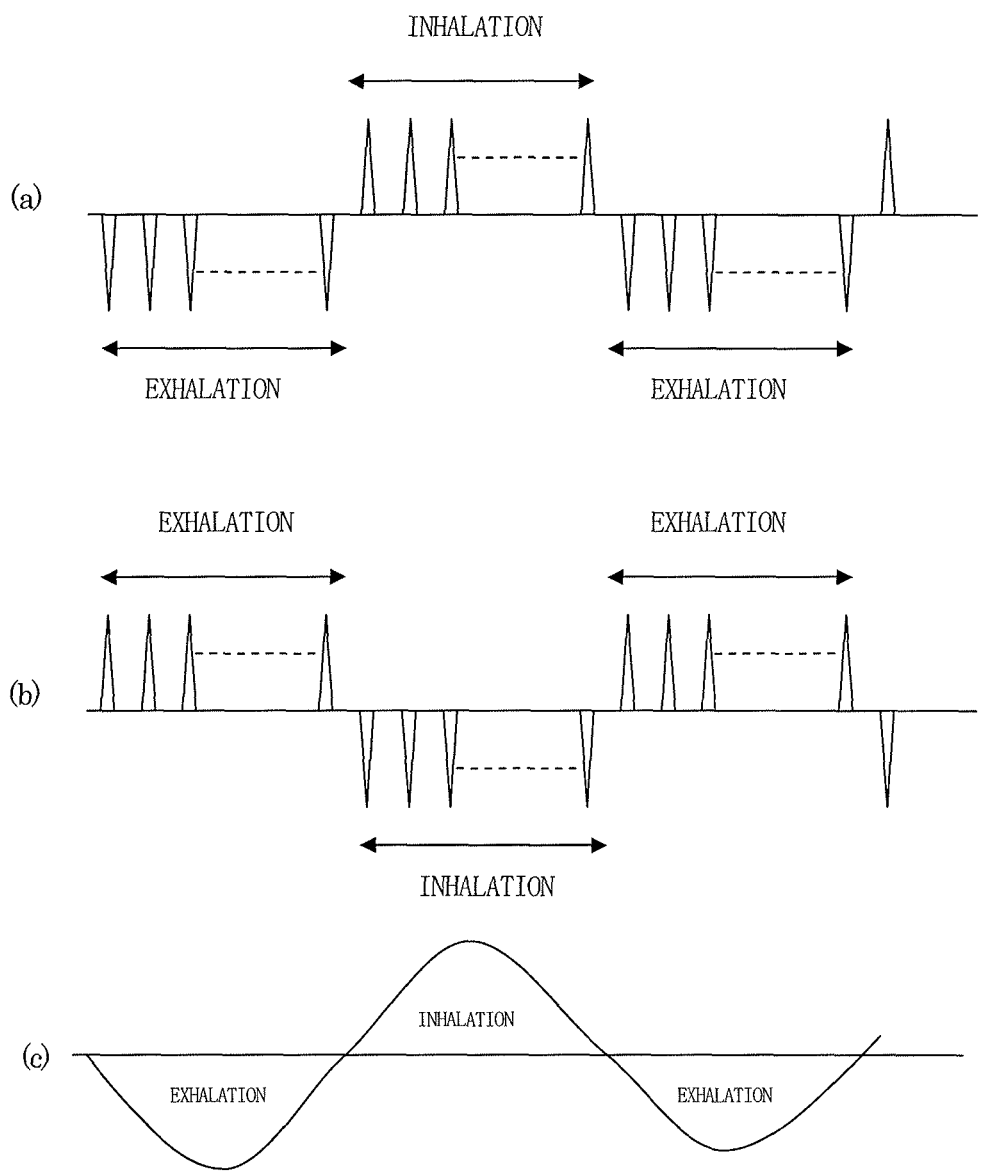
FIG. 4 is a diagram depicting an example in which pulse drive is executed by making pulses positive and negative separately in correspondence to the time of exhalation and the time of inhalation in the breathing impedance measuring apparatus according to the embodiment of the present invention.

A first method is to determine the direction of the pulse wave (upwardly projecting or downwardly projecting) to be identical with the direction of the flow in both exhalation periods and inhalation periods. This means that at the time of exhalation at which the flow curve (FIG. 4(c)) is in the negative area, the negative pulse wave is used, while at the time of inhalation at which the flow curve is in the positive area, the positive pulse wave is used. FIG. 4(a) depicts a case where the pulse wave's being positive and negative are switched in such a manner.

A second method is to determine the direction of the pulse wave (upwardly projecting or downwardly projecting) to be opposite to the direction of the flow in both exhalation periods and inhalation periods. This means that at the time of exhalation at which the flow curve (FIG. 4(c)) is in the negative area, the positive pulse wave is used, while at the time of inhalation at which the flow curve is in the positive area, the negative pulse wave is used. FIG. 4(b) depicts a case where the pulse wave's being positive and negative are switched in such a manner.

The control means 31 detects a point of time at which exhalation and inhalation switches, based on an output signal from the flow sensor 13. Because the output signal from the flow sensor 13 changes basically in a such manner as depicted in FIG. 4(c) in correspondence to breathing, the pulse wave's being positive and negative are switched at the zero-cross point, i.e., switching boundary, of the output signal from the flow sensor 13.

Figure 5:
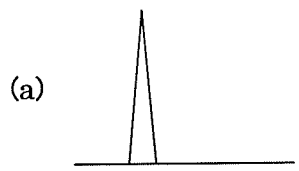
FIG. 5 is a diagram for explaining a process of generating by reverse computing an oscillation wave used in the breathing impedance measuring apparatus according to the embodiment of the present invention.
Figure 5:
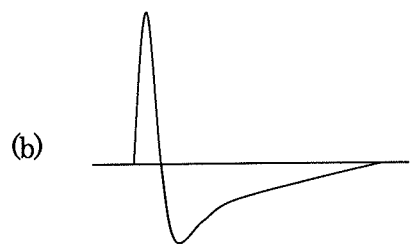
Figure 5:
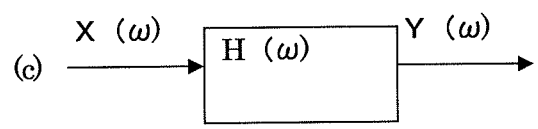
Figure 5:
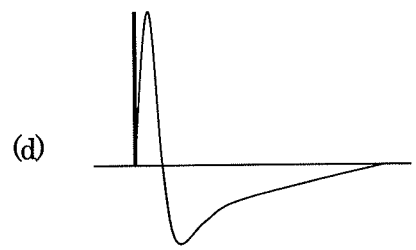
Figure 5:
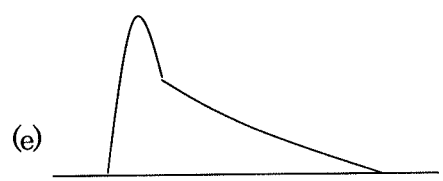

Specifically, for example, an operation of measurement using a triangular pulse will be described in detail. The following is an explanation of a positive pulse wave, and a negative pulse wave is subjected to the same process as the positive pulse wave is subjected to. When a triangular pulse shown in FIG. 5(a) is input to the loudspeaker 21 to drive it, an output signal from the loudspeaker 21 is a signal shown in FIG. 5(b) that has maximum points above and below its zero level. At this rime, a model shown in FIG. 5(c) is conceived. When a transmission function of the loudspeaker 21 is H ($\omega$), an input signal is X ($\omega$), and an output signal is Y ($\omega$), the following equation is given, from which x' (t) is obtained by reverse transformation to determine a signal represented by x' (t) to be a drive signal.

$$Y(\omega) = X(\omega) H(\omega) \qquad [\text{Eq. 1}]$$

Representing an input as X' ($\omega$) with which X ($\omega$) is obtained, (Equation 1)

$$X(\omega) = X'(\omega) H(\omega)$$
$$X'(\omega) = \frac{X(\omega)}{H(\omega)} = \frac{X(\omega)}{\frac{Y(\omega)}{X(\omega)}} = \frac{X^2(\omega)}{Y(\omega)}$$
$$x'(t) = F^{-1}(X'(\omega))$$

Practically, (Equation 2)

$$x'(t) = F^{-1}\left(\frac{X^2(\omega)}{Y(\omega) + A_0}\right)$$

Y($\omega$) obtained has no component that includes frequencies up to a high frequency and, therefore, x'(t) obtained from (Equation 1) is unstable. Therefore, as expressed in (Equation 2), a term obtained by adding a constant "$A_0$" to the denominator of X'(ω) is inversely Fourier-transformed and, thereby, x'(t) is obtained and is used as the driving signal. The signal x'(t) depicted in FIG. 5(e) may also be obtained by reverse-computing a signal formed by adding an impulse to an onset portion as depicted in FIG. 5(d) of an output signal of the loudspeaker 21 as depicted in FIG. 5(b).

Though the case for the triangular pulse is described in the above, as to a Hanning pulse, a signal may also be obtained by the reverse computation and this signal may also drive the loudspeaker 21.

As to which one of the pulse wave having a single frequency is used, an instruction may be given to the computer 30 using a keyboard, etc., not depicted and, in response to this, the control means 31 outputs a signal waveform selected thereby.

The Fourier transforming means 32, the extracting means 33, and the computing means 34 included in the computer 30 will be described. Under the pressurized condition in the oral cavity caused by a driving of the loudspeaker 21 as above, the Fourier transforming means 32 obtains signals using the pressure sensor 12 and the flow sensor 13, Fourier-transforms these signals obtained, and obtains a spectrum. A CIC filter 36 is provided in the pre-stage of the Fourier transforming means 32 and separates a breathing signal and an oscillation component obtained by the pressure sensor 12 and the flow sensor 13 from each other. The Fourier transforming means 32 takes out a signal using a Hanning window before the processing when necessary.

The extracting means 33 obtains a breathing high frequency component based on a spectrum that corresponds to a frequency component culled from the result of transformation by the Fourier transforming means 32, and extracts an oscillation wave component by subtracting the breathing high frequency component from a spectrum that corresponds to a frequency component left by the culling. In correspondence to the frequency culling, from spectra obtained by the Fourier transforming means 32, the breathing high frequency component is obtained based on a spectrum that corresponds to a frequency component other than a frequency component of n/T1 (n: integer), and the breathing high frequency component is subtracted from a spectrum that corresponds to the frequency component left by the culling (frequency component of n/T1) to extract the oscillation component.

As to the result of the extraction by the extracting means 33, the computing means 34 calculates respiratory impedance by dividing a pressure component by a flow component for each frequency. Representing the respiratory impedance as Z(ω), an oscillation wave component of the pressure in the oral cavity as P(ω), and an oscillation wave component of the flow as F(ω) and assuming that the respiratory impedance Z(ω) includes a resistance component R(ω) and a reactance component X(ω), the respiratory impedance Z(ω) is obtained using the following equations.

(Equation 3)

$$Z(\omega) = \frac{P(\omega)}{F(\omega)} = R + j\left(\omega L - \frac{1}{\omega C}\right) = R(\omega) + j(X)(\omega) \quad [\text{Eq. 2}]$$

The respiratory impedance Z(ω) obtained by the computing means 34 is converted into a display signal for a displaying unit 40 such as an LCD that is connected to the computer 30 and is output to the displaying unit 40 and, thereby, display is executed.

Operations by the respiratory impedance measuring apparatus configured as above will be described. In this example, the triangular pulse wave is selected and a measuring operation is started. The loudspeaker 21 is driven with the cycle of T second (for example, at intervals of 0.5 second) by the control means 31 and the signal input means 35 using the waveform obtained by the reverse computation.

Figure 6:
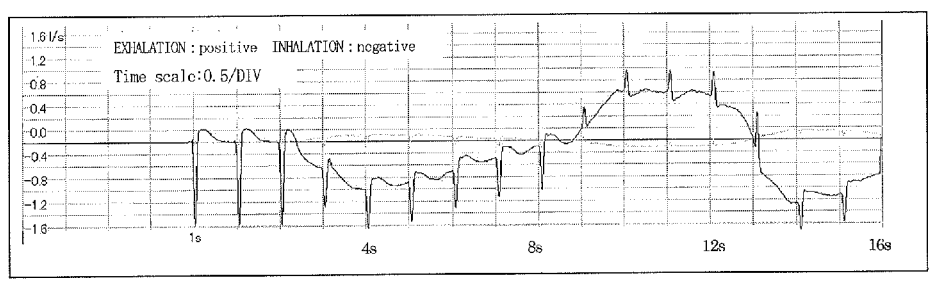
FIG. 6 is a diagram depicting a process of obtaining breathing impedance by the breathing impedance measuring apparatus according to the embodiment of the present invention, using the triangular pulse wave that is the oscillation wave.
Figure 6:
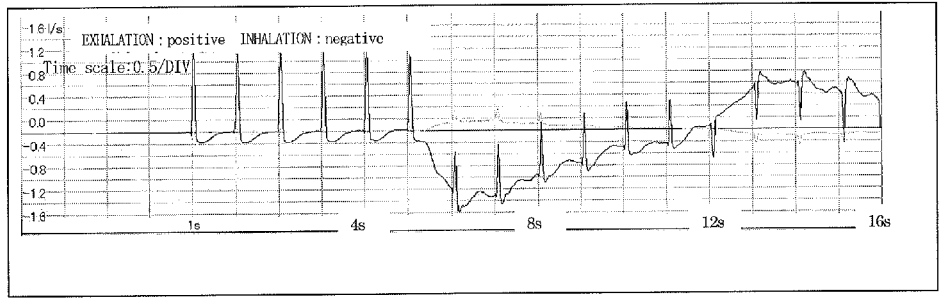
Figure 6:
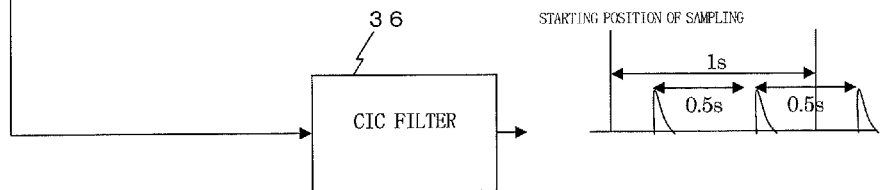
Figure 7:
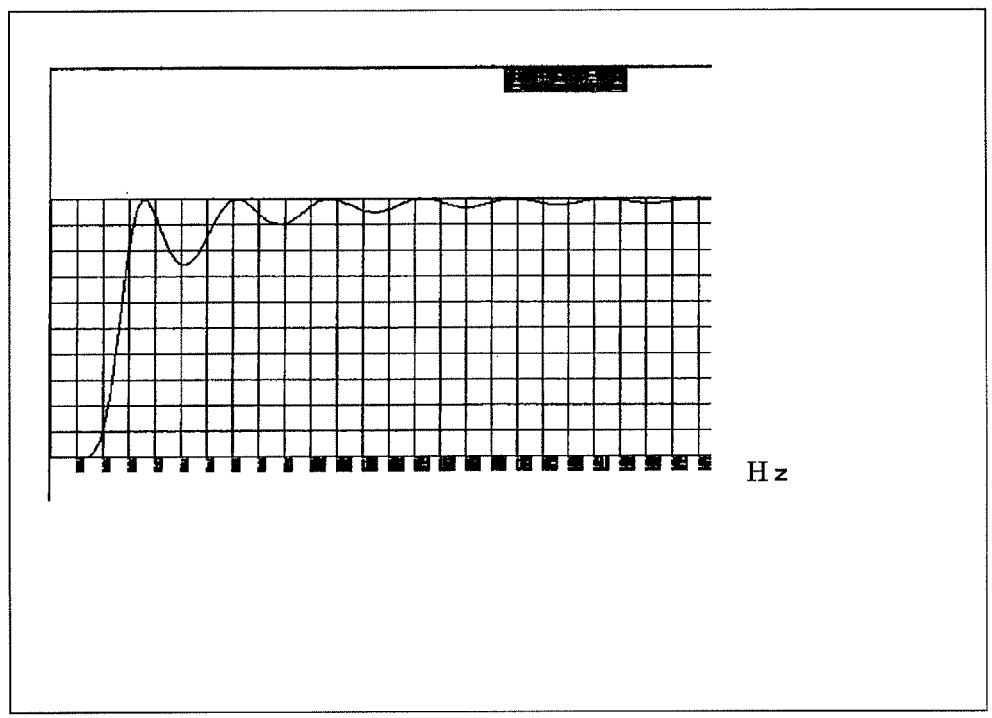
FIG. 7 is a diagram depicting the frequency characteristics of a filter used in the breathing impedance measuring apparatus according to the embodiment of the present invention.

At this time, both of the waveforms of the signals obtained by the pressure sensor 12 and the flow sensor 13 each are a waveform formed by superimposing the triangular pulse wave on the breathing signal as depicted in FIG. 6(a) or FIG. 6(b). This waveform is passed through the CIC filter 36 and the separation of the breathing wave and the oscillation wave (the triangular pulse wave) from each other is executed. FIG. 7 depicts the frequency property of the CIC filter 36. The CIC filter 36 may execute the separation without any shift of the phase. However, the breathing signal includes a high frequency component (the same frequency band as that of the oscillation signal) and, therefore, the separation may not be completely executed.

Figure 8:
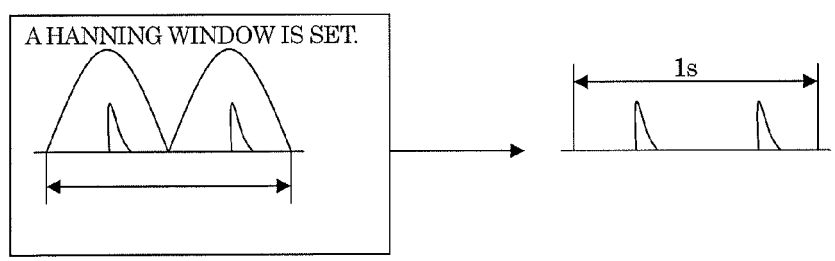
FIG. 8 is a diagram depicting the process of obtaining breathing impedance by the breathing impedance measuring apparatus according to the embodiment of the present invention, using the triangular pulse wave that is the oscillation wave.

Following the separation by the CIC filter 36, from the oscillation wave whose negative pulses are all reversed into positive pulses as shown in FIG. 6(c), a time span of 1 second (signal processing section $T_2$) between two inter-triangular-pulse middle points is taken out, and is used for signal processing. Subsequently, as shown in FIG. 8, each of pulses in the taken out $T_2$ section is processed by the Hanning window to take out the pulses.

Figure 9:
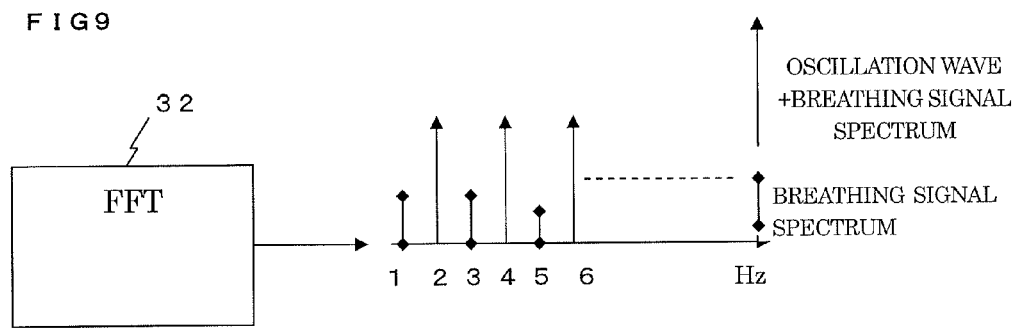
FIG. 9 is a diagram depicting the process of obtaining breathing impedance by the breathing impedance measuring apparatus according to the embodiment of the present invention, using the triangular pulse wave that is the oscillation wave.

Following the processing by the Hanning window, Fourier transformation by the Fourier transforming means 32 is executed to obtain a spectrum. In this obtained spectrum, for example, when $T_1$=0.5 second and $T_2$=1.0 second (usually $T_2$=m$T_1$ (m denotes an integer of 1 or larger)), an odd frequency spectrum 1, 3, 5, . . . that corresponds to a culled frequency component is a breathing signal spectrum that does not include an oscillation wave component, as shown in FIG. 9. An even frequency spectrum 2, 4, 6, . . . that corresponds to a frequency component left by the culling, on the other hand, includes the oscillation wave component and the breathing signal component.

Figure 10:
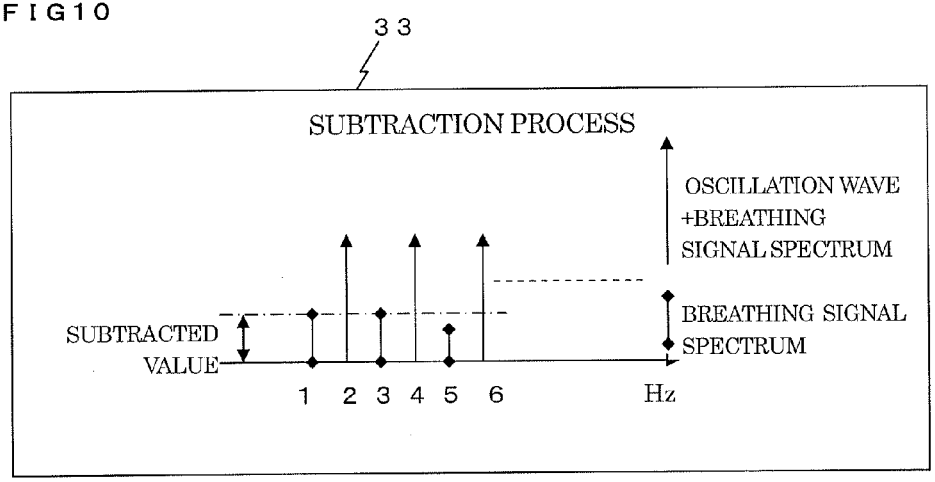
FIG. 10 is a diagram depicting the process of obtaining breathing impedance by the breathing impedance measuring apparatus according to the embodiment of the present invention, using the triangular pulse wave that is the oscillation wave.

As depicted in FIG. 10, the extracting means 33 subtracts a noise component that is estimated from the spectrum of the odd-number frequencies, from the spectrum of the even-number frequencies and, thereby, takes out the oscillation wave component.

The breathing high frequency signal that is equal to or higher than 3 Hz and that is conventionally considered not to be included in the breathing signal, is removed by the processing of the extracting means 33 and, therefore, high precision respiratory impedance measurement is enabled. The computing means 34 divides the pressure component by the flow component and, thereby, calculates the respiratory impedance as expressed by Equation (2) for each frequency for the result of the extraction by the extracting means 33. A display signal of the respiratory impedance calculated is created and is output to the displaying unit 40 and, thereby, display is executed.

Figure 11:
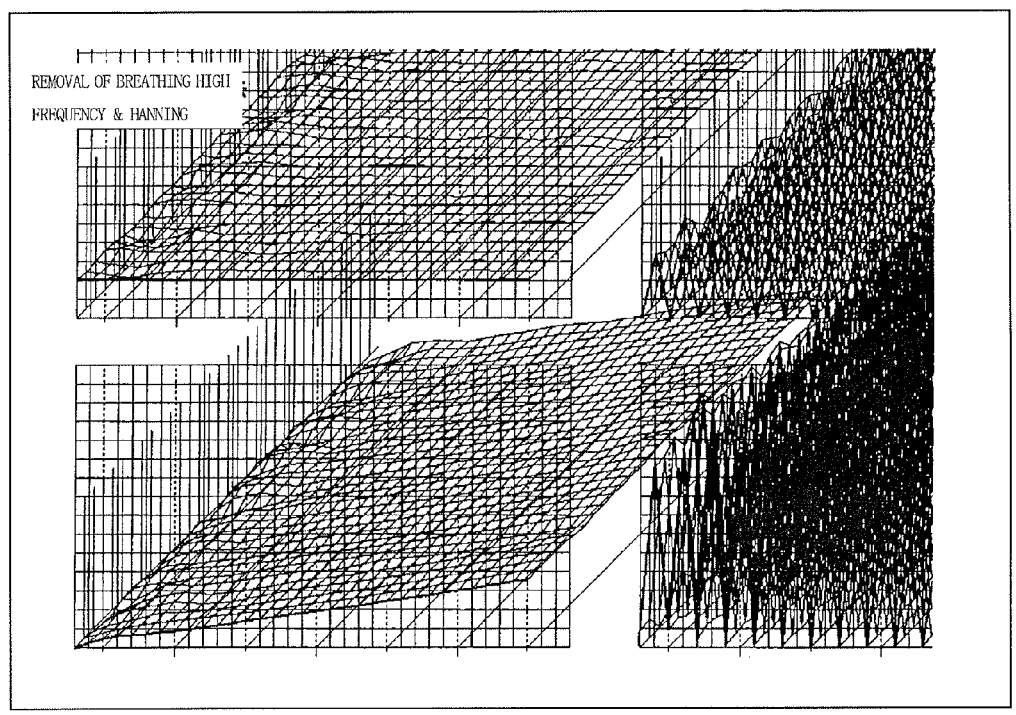
FIG. 11 is a diagram depicting breathing impedance obtained by the breathing impedance measuring apparatus according to the embodiment of the present invention.
Figure 12:
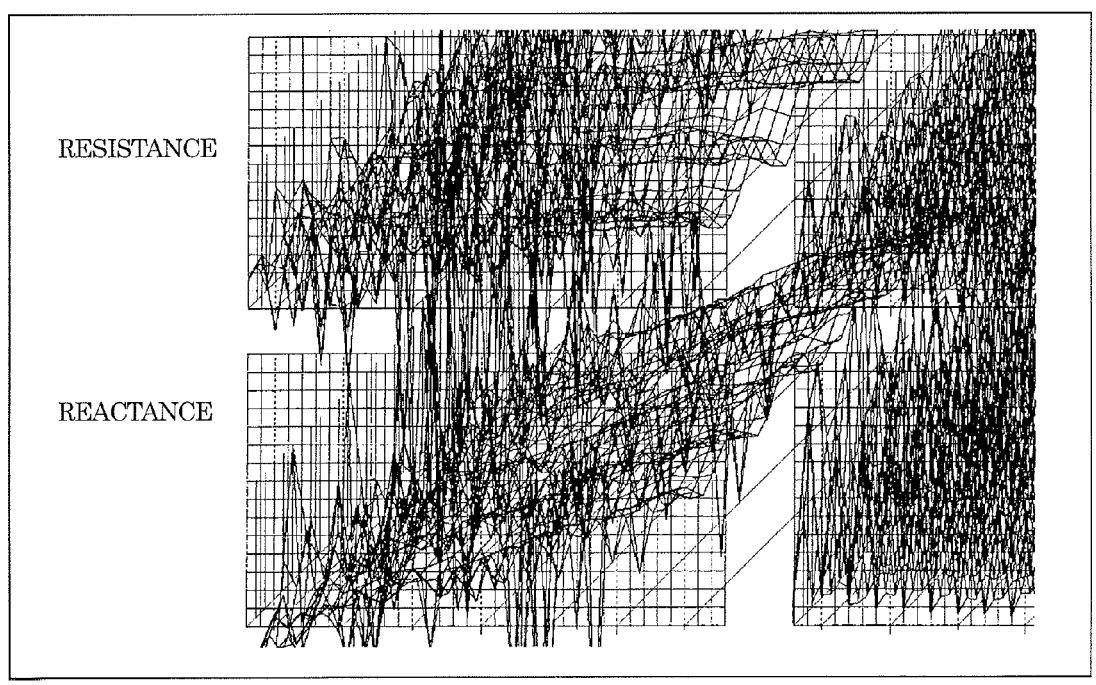
FIG. 12 is a diagram depicting breathing impedance obtained by a breathing impedance measuring apparatus not using the method of the present invention.

The respiratory impedance of a healthy person that is measured and displayed as above is depicted in FIG. 11. FIG. 12 depicts the respiratory impedance obtained when the breathing high frequency the removal of the breathing high frequency signal is not executed. In each of FIGS. 11 and 12, the axis of abscissa is a frequency axis whose one section of graduation corresponds to 1 Hz and the axis of ordinate represents the impedance. An oblique axis is the time axis. A genuine resistance portion is displayed in the upper portion of the diagram and a reactance portion is displayed in the lower portion of the diagram. In this case, by consecutively giving the triangular pulses at intervals of 0.5 second, display of new impedance appears one after another and the display is updated. Thereby, continuous measurement of the impedance is executed. As apparently seen from FIGS. 11 and 12, it is understood that the noise is removed and high precision respiratory impedance measurement is enabled. As apparent from the subtracting process by the extracting means 33, the component left by the subtraction is the even-number-frequency component of 2, 4, 6, . . . that corresponds to the frequency component left by the culling and, the odd-number-frequency component of 1, 3, 5, . . . that corresponds to the frequency component culled is not present. The computing means 34 executes an interpolating process and, thereby, respiratory impedance measurement is enabled for the component that is not present.

According to the embodiment of the present invention, the computing means 34 creates an image to be displayed on the displaying apparatus and executes display, thereby realizes the breathing impedance displaying method. Specifically, in displaying the breathing impedance computed by the computing means 34 as described above, the computing means 34, for example, sets the coordinates to take frequency values from the inside toward the this side on the screen (Y axis), takes out a resistance component Rrs for each of the frequencies to plot the resistance components Rrs in the direction of height of the displaying apparatus screen (Z axis), plots measurement time in the right direction on the screen (X axis), thus creates a three-dimensional image shown in FIG. 13 to display the image on the displaying apparatus. In other words, values are taken three-dimensionally, based on the impedance axis, frequency axis, and the time axis, to execute three-dimensional display.

In the above image creation, the image is created by including breathing impedance obtained by executing the interpolation process on the culled frequency in the three-dimensional value display to execute the display. For example, when an odd frequency is culled, two breathing impedance values that correspond to even frequencies adjacent to the culled odd frequency are obtained. The average of these two breathing impedance values is calculated to determine the calculated average to be a breathing impedance value that corresponds to the culled frequency. In this manner, because the result of the interpolation process is also displayed as an image, variation in breathing impedance values is minutely and smoothly displayed, which enables properly grasping breathing impedance for the whole of frequencies.

The time resolution of the signal processing is 0.5 second. As shown in FIGS. 13 to 16, the display is executed by creating an image whose length in the direction of the time axis is determined to be the length long enough to repeat therein at least two sets of exhalation and inhalation. In examples of FIGS. 13 to 16, the length in the direction of the time axis is determined to be the length long enough to repeat therein at least six sets of exhalation and inhalation. In this case, the display is executed by distinguishing periods of exhalation and periods of inhalation from each other by color as vertical strips of different colors at the background of the screen. In addition, a flow waveform (breathing signal waveform) BS obtained by the flow sensor 13 serving as a flow detecting means that detects an exhalation flow and an inhalation flow and the pressure sensor 12 is displayed together with the breathing impedance values.

Further, the display is executed by creating an image that expresses the magnitude of a breathing impedance value using variation in color and/(or) in light and shade. In FIGS. 13 to 16, images are created by coloring resistance values Rrs using a color scale CL shown on the lower side of each of FIGS. 13 to 16, and are displayed.

Images obtained by the above processes are displayed. While a test subject repeats resting breathing, such images as shown in FIGS. 13 to 16 are automatically created and displayed as time series images. In addition, these images may be visually observed as images that express changes in breathing impedance including breathing impedance that corresponds to a culled frequency using variation in color and/(or) in light and shade.

Figure 14:
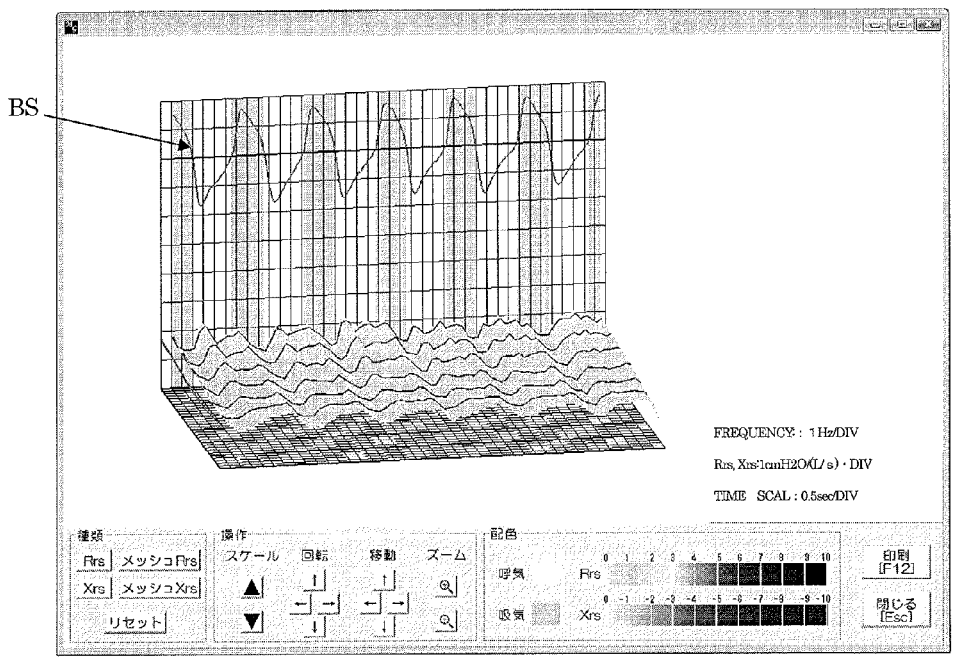
FIG. 14 is a diagram depicting one example in which breathing impedance by a healthy person is displayed using the breathing impedance measuring apparatus according to the embodiment of the present invention.
Figure 15:
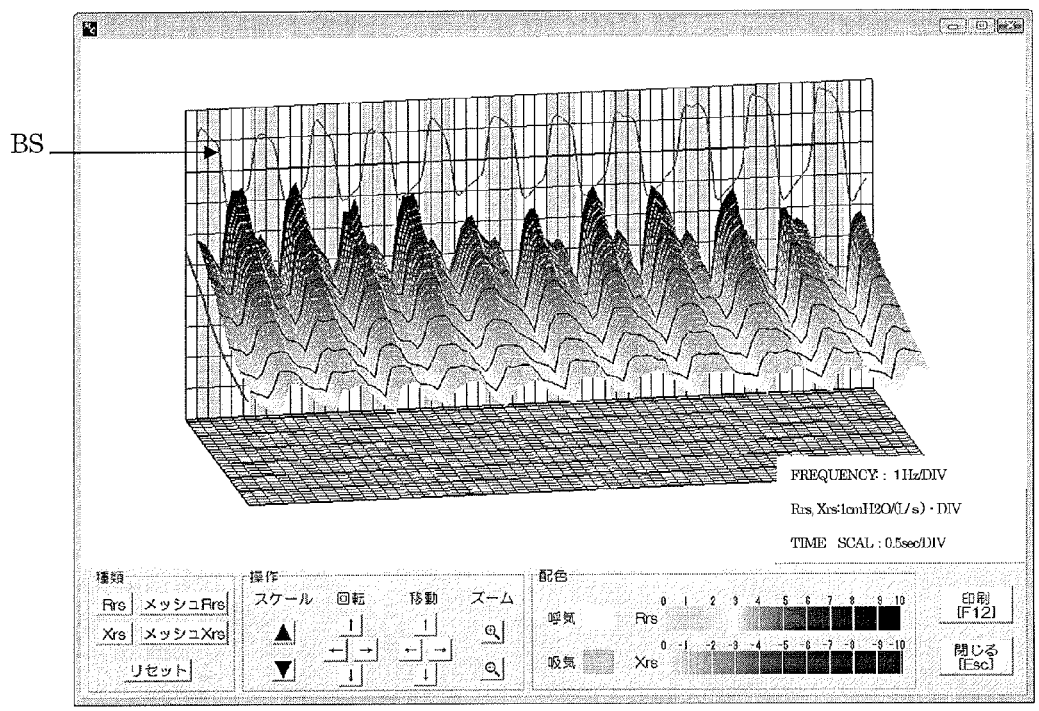
FIG. 15 is a diagram depicting one example in which breathing impedance by a COPD patient (stage 2) is displayed using the breathing impedance measuring apparatus according to the embodiment of the present invention.
Figure 16:
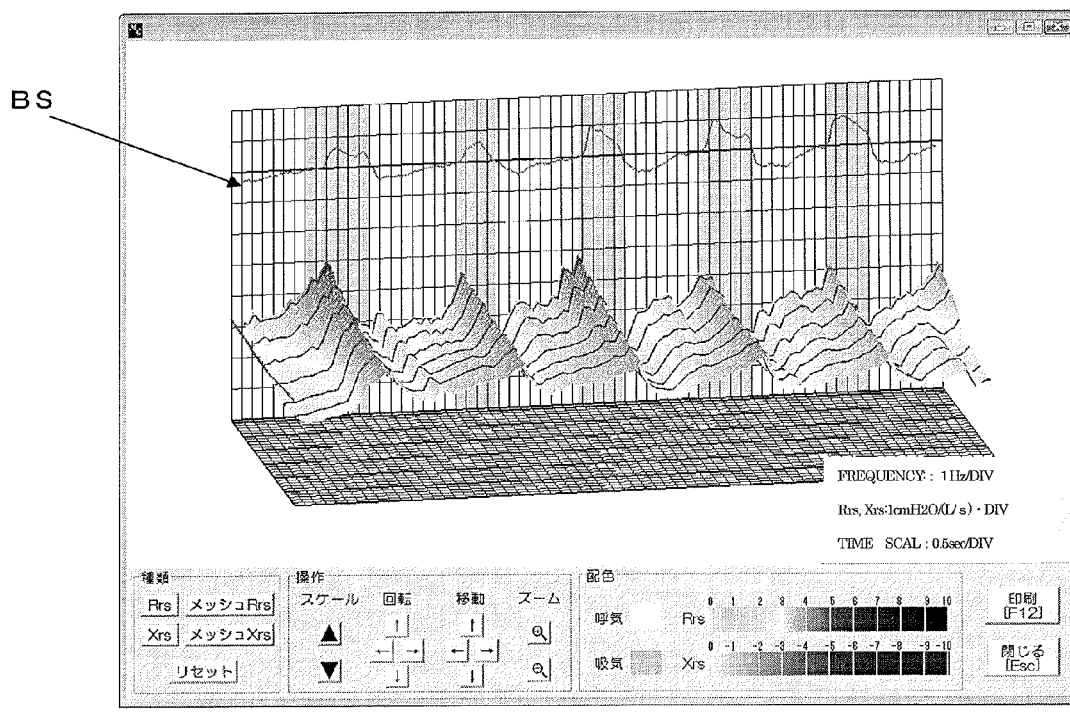
FIG. 16 is a diagram depicting one example in which breathing impedance by an asthma patient is displayed using the breathing impedance measuring apparatus according to the embodiment of the present invention.

Breathing resistance is the real part of measured breathing impedance, whose imaginary part is reactance. The apparatus of the this embodiment displays both breathing resistance and reactance as a three-dimensional color image, and makes it possible to observe the breathing resistance and reactance in comparison with the flow waveform BS (FIGS. 13 to 16). FIG. 14 depicts the result of the measurement carried out on a healthy person, FIG. 15 depicts the result of the measurement carried out on a COPD (Chronic Obstructive Pulmonary Diseases) patient, and FIG. 16 depicts a display example of the result of the measurement carried out on an asthma patient.

Figure 13:
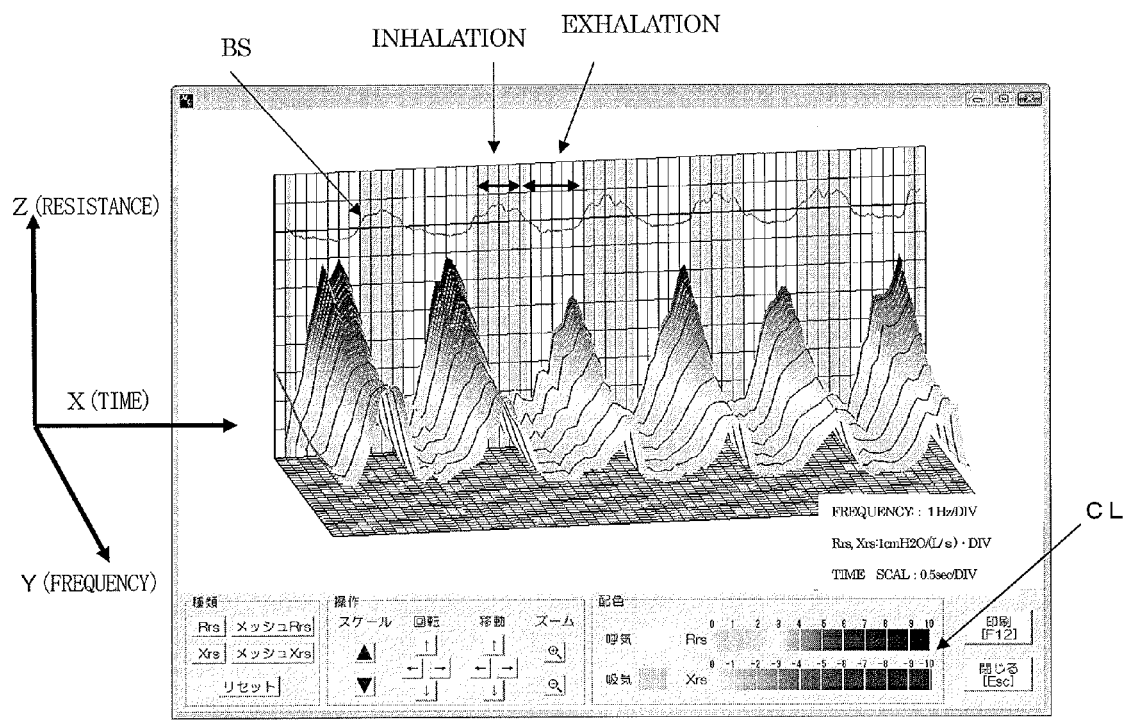
FIG. 13 is a diagram depicting one example in which breathing impedance by a COPD patient (stage 1) is displayed using the breathing impedance measuring apparatus according to the embodiment of the present invention.

FIG. 13 depicts a display example of the result of the measurement carried out on a COPD patient. In FIG. 13, breathing resistance in inhalation sections is displayed in green, which means that the breathing resistance is displayed in the color representing the same condition as a healthy person has. It is concluded, therefore, that the patient does not feel difficulty in breathing in the inhalation sections. Hence the patient is determined to be a patient suffering from COPD at stage 1. FIG. 15 depicts a display example of the result of the measurement carried out on a COPD patient. In FIG. 15, however, inhalation sections are painted with a color close to red, which indicates high resistance. The patient is, therefore, in a serious condition, thus determined to be a patient suffering from COPD at stage 2. In this manner, it is understood that by this displaying method (3D color graphic display), the frequency dependency and breathing cycle dependency of breathing impedance are expressed at the same time and determination of the normality and abnormality of the respiratory system as well as determination of the extent of abnormality may easily be carried out.

FIG. 13 depicting the image displayed by this embodiment, as described above, is an example of three-dimensional display of the breathing impedance of the COPD patient. In the display example of FIG. 13, the breathing resistance of inhalation is painted in green, thus displayed in the same color representing a healthy person's breathing resistance, but the breathing resistance of exhalation is displayed in red, which indicates that the breathing resistance values are extremely high. Therefore, it is confirmed from this measurement data (display) that a patient who shows the breathing impedance displayed in FIG. 13 has difficulty in exhalation. Medical information is known such that performing a bronchus CT scan on such a patient who has difficulty in inhalation to check the diameter of the patient's bronchus leads to a confirmation that the bronchus expands at the time of inhalation and contracts at the time of exhalation. This medical information is reported in a literature (Kurosawa, et al. N Engl J Med. 350:1036, 2004), etc. Hence an explanation is made that the breathing cycle dependency of the breathing resistance significantly reflects a change in the bronchus' diameter including its contraction. This fact can be confirmed by the apparatus of this embodiment, which is extraordinary beneficial to clinical practice.

Figure 17:
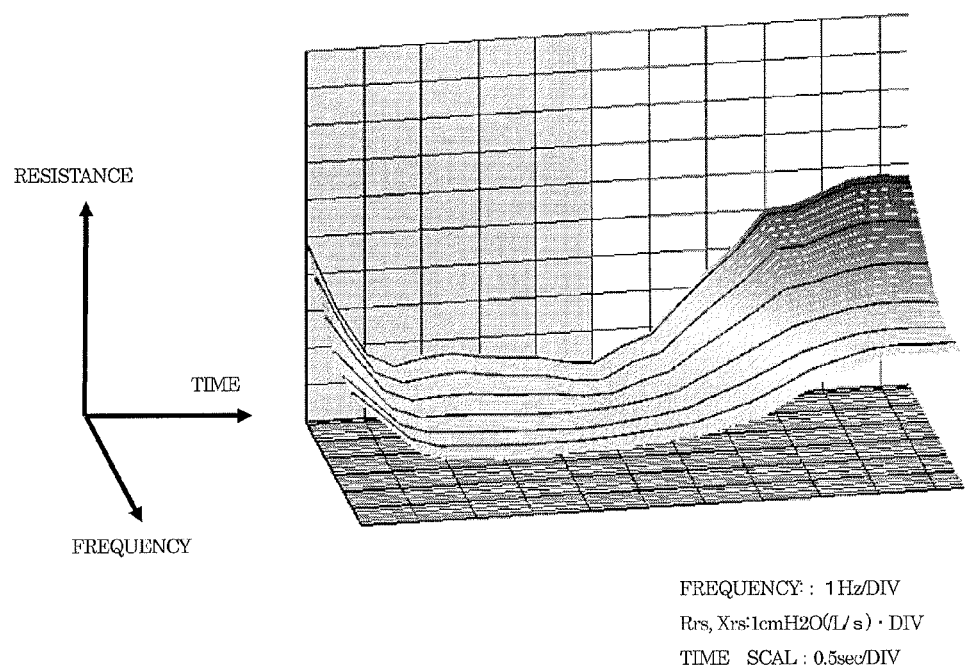
FIG. 17 is a diagram depicting one example in which signal averaging is carried out for each of cycles of breathing to determine averages and display the averages as a three-dimensional image, using the breathing impedance measuring apparatus according to the embodiment of the present invention.

Clinical medicine demands that these breathing impedance changes be expressed as numerical values using as few parameters as possible. According to the apparatus of this embodiment, the computing means 34 averages breathing impedance vales in a plurality of times of breathing for each elapsed time to determine averages, which are expressed as a three-dimensional image and are displayed on the displaying apparatus. Because breathing impedance slightly changes at every one cycle of breathing, signal averaging is carried out for every cycle of breathing to express averages as a three-dimensional image, which is displayed on the displaying apparatus, as shown in FIG. 17. This makes it possible to visually grasp average breathing impedance for one cycle of breathing, which is preferable for a case of comparative study, etc.

Figure 18:
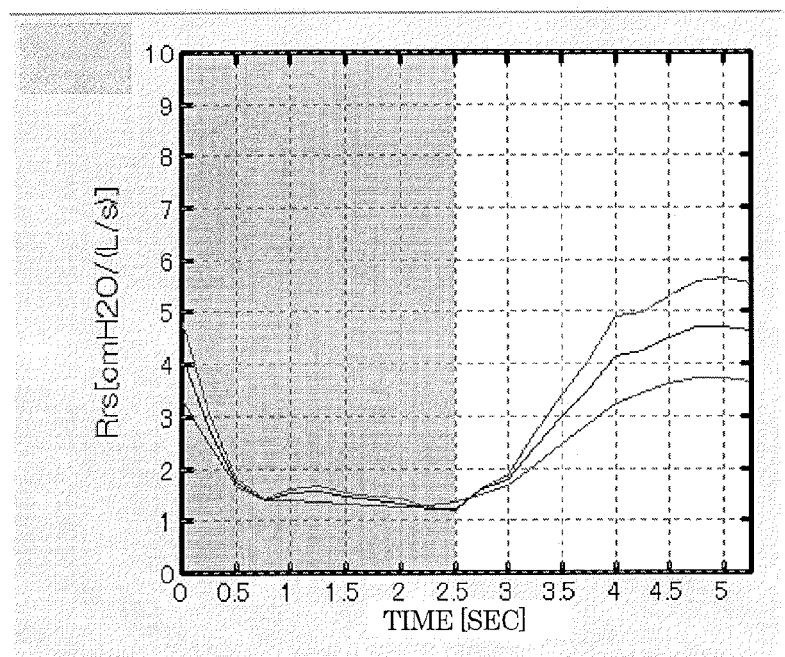
FIG. 18 is a diagram depicting one example in which based on the displayed three-dimensional image of FIG. 17, the averages at a given number of frequencies are each displayed as a line segment.

In addition, the computing means 34 displays each of the averages at a given number of frequencies as a line segment, and determines maximums, minimums, and differences between the maximums and the minimums at the given number of frequencies to display the determined maximums, minimums, and differences in the form of characters on the displaying apparatus. Examples of such display are shown in FIGS. 18 and 19. Specifically, the obtained signal averaging patterns are used to calculate time-dependent changes of typical resistance values from the averaging patterns at frequencies of 5 [Hz] and 20 [Hz] and a resonance frequency (expressed as res). The resonance frequency represents the frequency value at which reactance becomes zero ($X(\omega)=0$ in the equation (2)).

In actual display, R5 in green represents resistance values at 5 [Hz], R20 in red represents resistance values at 20 [Hz], and Rres in blue represents resistance values at the resonance frequency. The table of FIG. 19 indicates the minimums (min), the maximums (max), and the differences (sub) between the minimums and the maximums of those resistance values in breathing cycles. These numerical values signify the physiological condition of a living body, and are, therefore, extraordinary beneficial to clinical practice. In the table of FIG. 19, Fres denotes the resonance frequency.

The computing means 34 exerts its function, for example, to display the average breathing impedance for each one cycle of breathing shown in FIG. 17 on the left half of one screen, the graph of FIG. 18 on the upper part of the right half of one screen, and the table of FIG. 19 on the lower part of the right half of one screen. Through such display, the variation tendency of the breathing impedance is grasped using displayed average values and graphs while actual numerical values are checked by referring to tables. Hence such display may be used effectively in a clinical scene, etc.

EXPLANATION OF LETTERS OR NUMERALS

11 tube
12 pressure sensor
13 flow sensor
21 loudspeaker
30 computer
31 control means
32 Fourier transforming means
33 extracting means
34 computing means
35 signal input means
36 CIC filter
40 displaying unit

The invention claimed is:

1. A respiratory impedance measuring apparatus comprising:
    a pressurizing means for applying an air vibration pressure to inside of an oral cavity;
    a pressure detecting means for detecting pressure signals inside of an oral cavity;
    a flow detecting means for detecting flow signals generated by breathing;
    a timing detecting means for detecting time points at which exhalation and inhalation switches, based on output signals from the flow detecting means;
    a pulse signal generating means for generating pulse signals of a predetermined frequency, wherein the pulse signals are switched between positive and negative based on the time points;
    a control means for controlling the pressurizing means by using the pulse signals generated by the pulse signal generating means, and generating the air vibration pressure by oscillation waves of the pulse signals, wherein the predetermined frequency of the pulse signals generated by the pulse signal generating means is greater than a frequency of the flow signals generated by breathing;
    a Fourier transforming means for obtaining Fourier transform spectrums by Fourier transforming the pressure signals and the flow signals;
    an extracting means for obtaining first spectrums that contain oscillation wave components and respiratory signal components from the Fourier transform spectrums of the pressure signals and the flow signals, extracting second spectrums that contain the respiratory signal components from the Fourier transform spectrums of the pressure signals and the flow signals, and obtaining the oscillation wave components by subtracting the second spectrums from the first spectrums; and
    a computing means configured for obtaining respiratory impedance by dividing the oscillation wave components of the Fourier transform spectrums of the pressure signals with the oscillation wave components of the Fourier transform spectrums of the flow signals for each frequency of the Fourier transform spectrums of the pressure and flow signals.

2. The respiratory impedance measuring apparatus of claim 1, wherein
    the control means generates the air vibration pressure by the oscillation wave having only $n/T_1$ (n: an integer, $T_1$: a real number) frequency components, by using pulse waves having a cycle of $T_1$.

3. The respiratory impedance measuring apparatus of claim 1 or 2, wherein
    the control means includes a signal input means that supplies an input signal to the pressurizing means such that an oscillation wave having a desired pressure waveform is an output signal, based on reverse computation using an input signal and an output signal of the pressurizing means and a transfer function of the pressurizing means.

4. The respiratory impedance measuring apparatus of claim 3, wherein
    the signal input means supplies to the pressurizing means as an input signal a signal obtained by adding a specific value to each of frequency components of the signal obtained by the reverse computation, or by reverse computing a signal formed by adding an impulse to an onset portion of the output signal.

5. The respiratory impedance measuring apparatus of claim 2, wherein
    signal processing is carried out in a signal processing section $T_2$ ($T_2=mT_1$ (m denotes an integer of 1 or larger)).

6. A respiratory impedance measuring method comprising:
    a pressurizing step of applying an air vibration pressure to an inside of an oral cavity by using a pressurizing means;

a flow detecting step for detecting flow signals generated by breathing by using a flow detecting means;

a pressure detecting step of detecting pressure signals inside of an oral cavity by using a pressure detecting means;

a timing detecting step of detecting time points at which exhalation and inhalation switches, based on output signals from the flow detecting step by using a timing detecting means;

a pulse signal generating step of generating pulse signals of a predetermined frequency, wherein the pulse signals are switched between positive and negative based on the time points by using a pulse signal generating means;

a controlling step, by using a control means, of controlling the pressurizing step by using the pulse signals generated by the pulse signal generating step, and generating the air vibration pressure by oscillation waves of the pulse signals, wherein the predetermined frequency of the pulse signals generated by the pulse signal generating step is greater than a frequency of the flow signals generated by breathing;

a Fourier transforming step of obtaining Fourier transform spectrums by Fourier transforming the pressure signals and the flow signals by using a Fourier transforming means;

an extraction step of obtaining first spectrums that contain oscillation wave components and respiratory signal components from the Fourier transform spectrums of the pressure signals and the flow signals, extracting second spectrums that contain the respiratory signal components from the Fourier transform spectrums of the pressure signals and the flow signals, and obtaining the oscillation wave components by subtracting the second spectrums from the first spectrums by using an extraction means; and a computing step, by using a computing means, configured for obtaining respiratory impedance by dividing the oscillation wave components of the Fourier transform spectrums of the pressure signals with the oscillation wave components of the Fourier transform spectrums of the flow signals for each frequency of the Fourier transform spectrums of the pressure and flow signals.

7. The respiratory impedance measuring method of claim 6, wherein the control step generates the air vibration pressure by the oscillation wave having only $n/T_1$ (n: an integer, $T_1$: a real number) frequency components by using pulse waves having a cycle of $T_1$.

8. The respiratory impedance measuring method of claim 6 or 7, wherein the control step comprises a signal input step that supplies an input signal to the pressurizing step such that an oscillation wave having a desired pressure waveform is an output signal, based on reverse computation using an input signal and an output signal for the pressurizing step and a transfer function of the pressurizing step.

9. The respiratory impedance measuring method of claim 8, wherein the signal input step supplies to the pressurizing step as an input signal a signal obtained by adding a specific value to each of frequency components of the signal obtained by the reverse computation, or by reverse computing a signal formed by adding an impulse to an onset portion of the output signal.

10. The respiratory impedance measuring method of claim 7, wherein signal processing is carried out in a signal processing section $T_2$ ($T_2=mT_1$ (m denotes an integer of 1 or larger)).

* * * * *